United States Patent [19]

Brown

[11] Patent Number: 5,569,212

[45] Date of Patent: Oct. 29, 1996

[54] APPARATUS FOR ELECTRICALLY DETERMINING INJECTION DOSES IN SYRINGES

[75] Inventor: Stephen J. Brown, Palo Alto, Calif.

[73] Assignee: Raya Systems, Inc., Mountain View, Calif.

[21] Appl. No.: 278,929

[22] Filed: Jul. 22, 1994

[51] Int. Cl.$^6$ ................................................ A61M 5/00
[52] U.S. Cl. .................... 604/207; 604/208; 604/218; 123/DIG. 1
[58] Field of Search ..................... 604/154, 207, 604/208, 218, 187; 123/DIG. 1

[56] References Cited

U.S. PATENT DOCUMENTS

| 4,950,246 | 8/1990 | Muller | 604/154 |
| 5,176,502 | 1/1993 | Sanderson et al. | 417/18 |

Primary Examiner—Randall L. Green
Assistant Examiner—A. T. Nguyen
Attorney, Agent, or Firm—Lumen Intellectual Property Services

[57] ABSTRACT

An apparatus for electrically determining and recording the dose of an agent delivered with a syringe consisting of a barrel for holding the agent and a plunger for expelling the agent. The syringe has a conducting path with an input terminal and an output terminal, and at least one electrically resistive element, whose resistance changes depending on the position of the plunger inside the barrel. The apparatus produces a voltage difference across the terminals and causes an electric current to flow through the conducting path. An electric response measuring device, preferably an ammeter, measures the electric current delivered from the syringe's output terminal and calculates the dose therefrom. The result is recorded by a digital memory unit.

10 Claims, 3 Drawing Sheets

APPARATUS FOR ELECTRICALLY DETERMINING INJECTION DOSES IN SYRINGES

BACKGROUND—FIELD OF THE INVENTION

The present invention relates to the field of injection syringes, and in particular to an apparatus for measuring injection doses in syringes with electricity.

BACKGROUND—DESCRIPTION OF PRIOR ART

Injection syringes are most commonly used for administering medicines in human patients, e.g., influenza vaccines, insulin, and many others. The dose of active agents delivered in these situations has to be carefully monitored and recorded. This is especially true when the patient has to take multiple injections. In self-care therapies, e.g., self-management of diabetes, patients themselves perform the injections and keep records. However, because of the frequency of such injections, often several times a day for diabetes, it becomes difficult to keep accurate records. Indeed, studies have shown that patients own records and recollections are often incomplete and inaccurate. In the long-term this makes patient monitoring impossible and jeopardizes the therapy, possibly even endangering the patients life. The problem is especially acute for diabetic patients, who have to be very careful about insulin dosing.

U.S. Pat. No. 5,009,645 issued to Jules Silver on Apr. 23, 1991 describes a disposable syringe with an adjustable stop mechanism. This mechanism consists of a knife edge which embeds itself into a specified location of a rail section located axially outside the syringe barrel. In this manner the volume of medication to be delivered during the subsequent injection is preset. Another solution involves a rotatable cap mechanism cooperating with a rotatable plunger. The mechanism for presetting an injection dose in this manner have been described in, e.g., U.S. Pat. No. 5,104,380 issued to Rury Holman et al. on Apr. 14, 1992 and U.S. Pat. No. 5,226,895 issued to Harris Dale on Jul. 13, 1993. There are also other types of mechanisms for presetting an injection volume in a syringe.

Unfortunately, none of these directly address the problem of recording when and how much medication was injected over the course of a long-term treatment involving a large number of injections. That is because once a syringe is empty the patient has to use another syringe or, in some cases, refill the original one, and is still burdened with the task of keeping track of the total drug volume administered from the previous syringe.

U.S. Pat. No. 4,853,521 issued to Claeys Ronald on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps, e.g., weighing syringes, scanning in bar codes, etc. These complex procedures precludes effective home use. In addition, the apparatus is too expensive.

Thus, no cost-effective, efficient, and accurate apparatus exist for recording dosages delivered from many syringes over a period of time.

OBJECTS AND ADVANTAGES OF THE INVENTION

In view of the above, it is an object of the present invention to provide an apparatus for determining and recording doses of medicine delivered from an injection syringe accurately and inexpensively. Another object of the invention is to suit the apparatus to diabetic patients in particular.

These and other objects and advantages will become more apparent after consideration of the ensuing description and the accompanying drawings.

SUMMARY OF THE INVENTION

The apparatus of the invention overcomes the disadvantages of prior art by determining and recording the dose of an agent delivered with a syringe comprising a barrel for holding said agent and a plunger for expelling said agent rapidly and in a simple manner. The apparatus comprises a conducting path for conducting an electric current through the syringe. The conducting path comprises an input terminal at a first end of the conducting path for receiving the electric current, an output terminal at the other end of the conducting path for giving off the electric current, and at least one electrically resistive means. The voltage for producing a voltage difference across the input and output terminals and causing the electric current to flow through the conducting path is supplied by a voltage generating means. An electric response measuring means external to the syringe measures the electric current given off from the output terminal and calculates the dose from this electric current. The result is recorded by a recording means.

In a push plunger syringe the resistive means can consist of a resistive strip mounted along the plunger in the conductive path. In a rotatable plunger syringe the resistive means can consist of a potentiometer mounted in the cap and changing its resistance as the cap is rotated. The change in resistance produced by the advance of the plunger or rotation of the cap is measured through the change in electrical current using an ammeter. The results are recorded in a digital memory unit. For convenience, the apparatus can be integrated into medical devices such as a blood glucose meter.

Alternatively, the conducting path contains an inductive element, e.g. a solenoid, for generating a magnetic field, and the plunger contains a magnetically responsive element, such as a core made of paramagnetic or diamagnetic material. The magnetic response to the current caused by the applied voltage is measured with the aid of a measuring loop made of a conducting material and a meter for measuring magnetically induced voltage connected to measure the induced voltage in the loop.

Finally, the conducting path can also include a capacitive element, such as conducting plates mounted on the plunger and the barrel, for accumulating an electric charge. The change in capacitance caused by the advance of the barrel is measured in the conventional way with a capacitance measuring circuit.

DESCRIPTION

Figure 1:
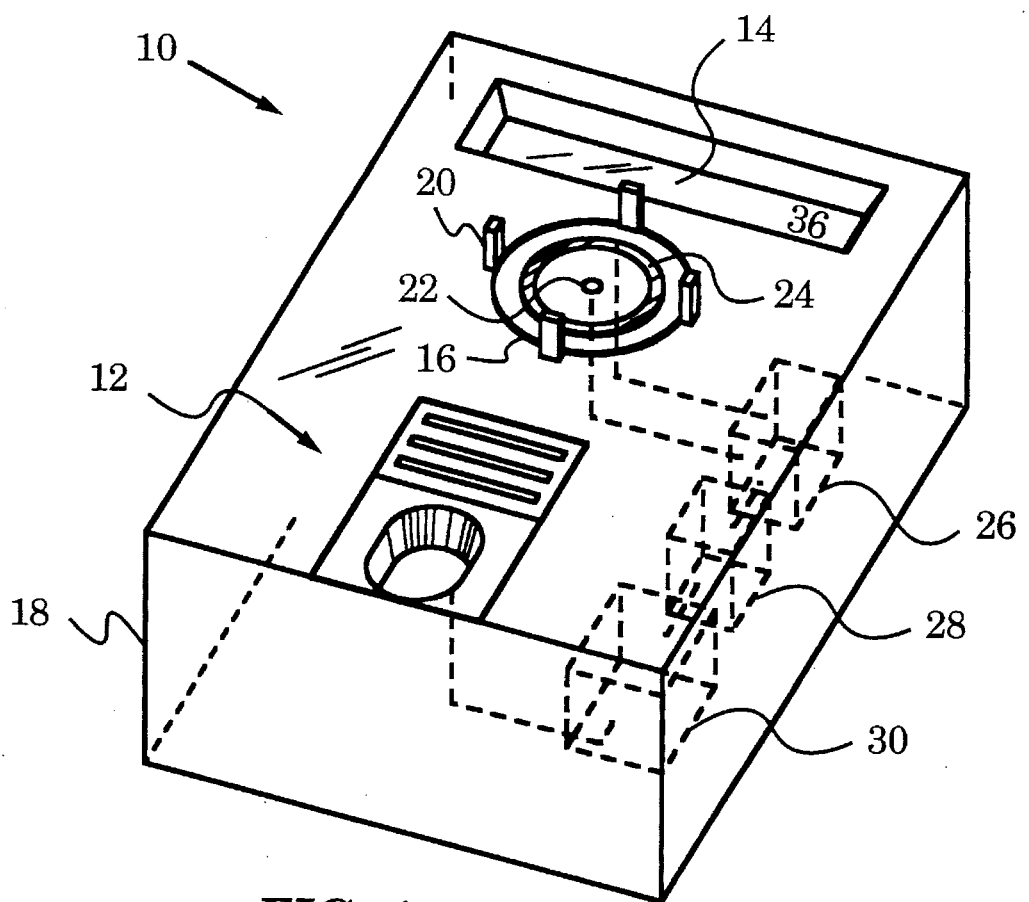
FIG. 1 is a three dimensioned view of a conventional blood-glucose meter equipped with a portion of the apparatus according to the invention.

In the preferred embodiment a portion of the apparatus of the invention is incorporated into a blood glucose meter 10 as shown in FIG. 1. The standard part of glucose meter 10 includes a conventional blood glucose measuring assembly 12 for collecting blood from a patient's finger and a display 14 for displaying the results. In addition, meter 10 has a circular field 16 delineated on a face plate 18 below display 14. Circular field 16 is bordered on four sides by rigid positioning studs 20. The size of circular field 16 corresponds to the dimensions of a cap of an injection syringe. Positioned concentrically inside circular field 16 are a circular input contact 22 and a ring-shaped output contact 24. Both contacts 22, 24 are made of a conducting material, e.g., copper.

Below face plate 18 contacts 22 and 24 are connected to a voltage generator 26 and an ammeter 28 as indicated. Voltage generator 26 is thus connected to apply a voltage difference between input contact 22 and output contact 24. Typically, the voltage generated by generator 26 is on the order of 1 to 20 volts. Meanwhile, ammeter 28 is set up to measure a current flowing between contacts 22 and 24 during the measuring process as described below. Finally, an electronic memory 30 is connected to ammeter 28. Memory 30 is connected to record the current readings of ammeter 28.

Figure 2A:
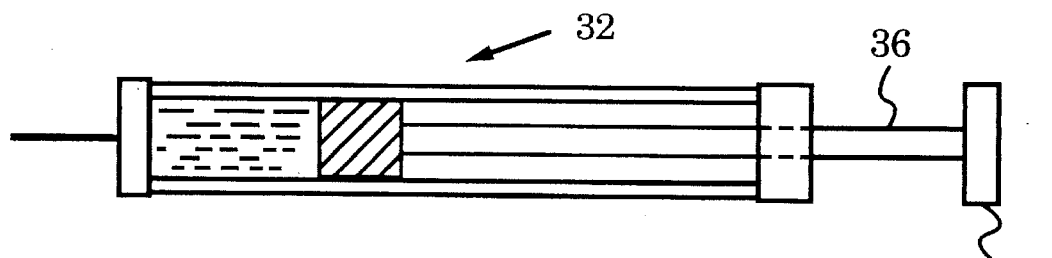
FIG. 2A is a side view of a conventional, injection syringe.
Figure 2B:
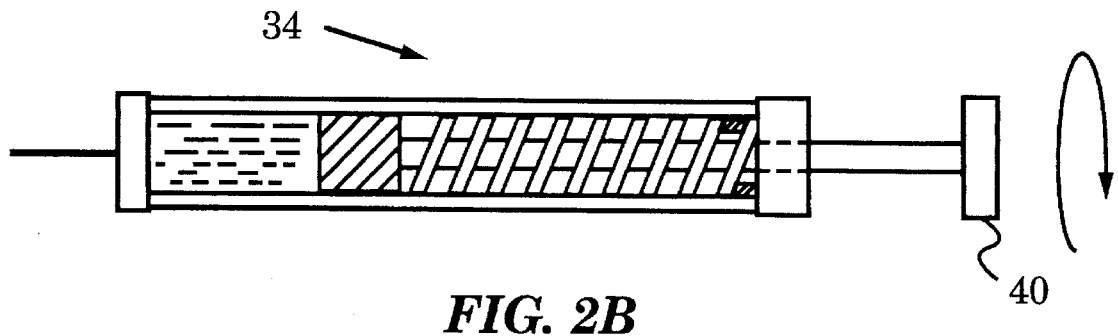
FIG. 2B is a side view of another conventional, injection syringe with a screw-top dosage selector.

FIGS. 2A and 2B show two standard syringes 32 and 34. Syringe 32 has a push-type plunger 36 which is advanced by a direct force exerted on a cap 38. Meanwhile, syringe 34 has a rotatable cap 40 enabling the user to preset a dose with a mechanism (not shown) as disclosed in U.S. Pat. No. 5,104,380 or U.S. Pat. No. 5,226,895. The apparatus of the invention can be advantageously employed in both types of syringes.

Figure 3:
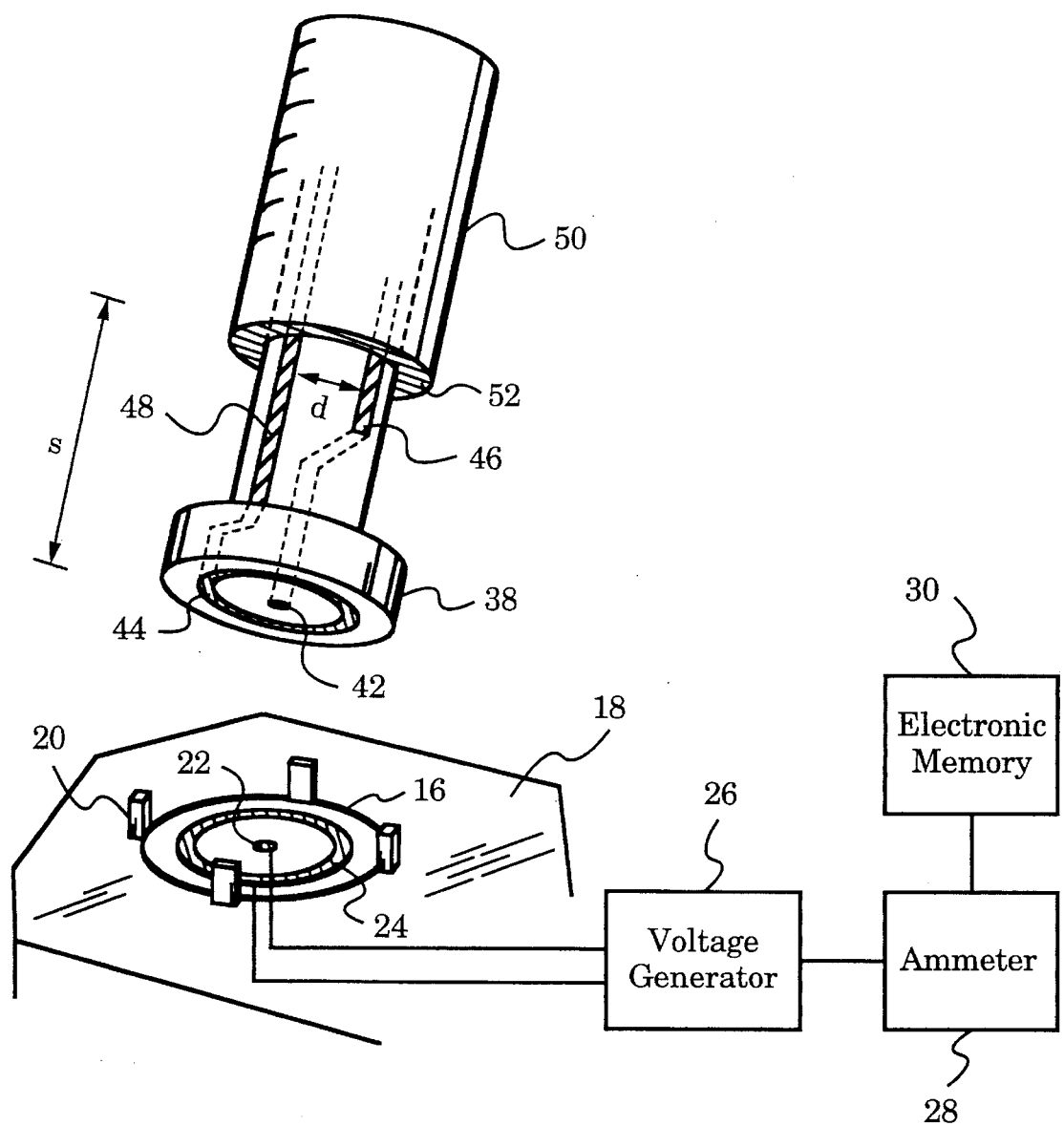
FIG. 3 is a side view and a partial block diagram of the meter from FIG. 1 illustrating how an injection syringe according to the invention is placed for dose measurement.

For clarity, corresponding parts will be designated by the same reference numbers. FIG. 3 illustrates in detail the positioning of cap 38 of syringe 32 on circular field 16 for dose measurement. Cap 38 is circular and corresponds in size to circular field 16, such that positioning studs 20 fit exactly around the cap's circumference. Positioned concentrically on the surface of cap 38 are a circular input terminal 42 and a ring-shaped output terminal 44. Both terminals 42, 44 are made of a conducting material, e.g., copper, and are designed to come in full contact with contacts 22, 24 respectively when cap 38 is pressed against field 16. Inside syringe 32 terminals 42 and 44 are connected to conducting strip 46 and a resistive strip 48 respectively. In the preferred embodiment resistive strip 48 is made of a material whose resistivity (resistance per unit length) is many orders of magnitude larger than the resistivity of conducting strip 46. For example, the resistivity of conducting strip 46 is 1 Ohm/m and the resistivity of resistive strip 48 is 1,000 Ohm/m.

A short portion, typically about 5 to 10 mm, of conducting strip 46 passes inside plunger 36, e.g., it is moulded into the plastic of the plunger, and then strip 46 emerges on the surface of plunger 36. Similarly, resistive strip 48 is also routed inside cap 38 and then emerges on the surface of plunger 36 parallel with conducting strip 46 at a distance d away. Distance d is chosen to ensure that no current can bridge over from strip 46 to strip 48. A barrel 50 containing the medicine to be injected is located above cap 38. A rim 52 surrounds and contacts plunger 36 as well as strips 46 and 48 circumferentially at the location where plunger 36 enters barrel 50.

Rim 52 is lined with a conducting material, e.g., copper. Some of the conducting material wraps inside barrel 50 to ensure a good electrical contact with strips 46 and 48. This creates a conducting path (42, 46, 52, 48, 44) from terminal 42 to terminal 44. The length of this conducting path depends on the distance s between cap 38 and rim 52. Its total length approximately equals to $2s+d$. In other words, the length of the conducting path decreases the further plunger 36 advances inside barrel 50.

Figure 4:
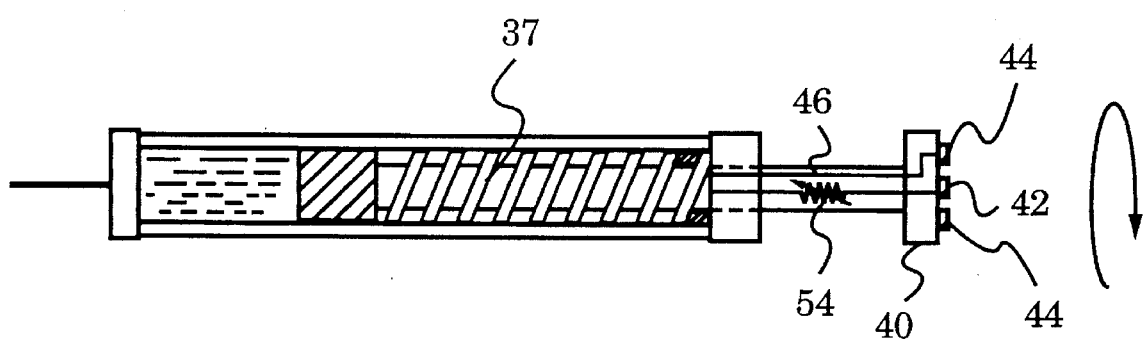
FIG. 4 is a sectional side view of an injection syringe according to the invention for dose determination by resistance measurements.

FIG. 4 shows an alternative embodiment of the invention designed for rotatable plunger syringe 34. Here resistive strip 48 is replaced by a potentiometer 54. Rotatable cap 40 is mechanically joined to potentiometer 54 such that when cap 40 is twisted potentiometer 54 is rotated by the same amount. It is obvious to any person skilled in the art how to perform such a mechanical connection. Suitable potentiometers are commercially available.

OPERATION

To perform a measurement and record the amount of dispensed medication the patient first places cap 38 of syringe 32 on circular field 16 as shown in FIG. 3 before administering the medication. When cap 38 is properly placed between positioning studs 20 input contact 22 and output contact 24 are aligned with input terminal 42 and output terminal 44.

Meanwhile, a well-known voltage V is generated by voltage generator 26. This voltage is applied across input terminal 42 and output terminal 44. Voltage V causes a current I to flow through the conducting path consisting of input terminal 42, conducting strip 46, rim 52, resistive strip 48, and output terminal 44. Based on Ohm's law, which states that $I = V/R$, current I is inversely proportional to the total resistance R of the conducting path. Meanwhile, this total resistance R depends on the length of the conductive path, which was shown to equal approximately $2s+d$. Of this distance s is the length of resistive strip 48. Since the resistance of conducting strip 46 and rim 52 are very small in comparison to the resistance of strip 48 an approximation is made. The total resistance of the conducting path is taken to be the resistance constituted by length s of resistive strip 48, the resistance of the other parts of the path being negligible. Thus R is computed by multiplying the resistivity of strip 48 times distance s.

In this manner total resistance R of the conducting path is related to how far plunger 36 is residing inside barrel 50 at the time of measurement. Consequently, a measurement of current I, which depends on total resistance R, produces electrical data corresponding to how far plunger 36 is located inside barrel 50. This measurement is performed by ammeter 28 and stored in memory 30.

In the preferred embodiment the measurement is internally converted by an electronic microprocessor (not shown)

into a "dose remaining" measurement and displayed on display 14. This alerts the patient that the injection can now be performed. After injecting the prescribed amount of medication (which may be displayed on display 14 in a particularly advantageous embodiment) the patient repeats the above procedure to get a new "dose remaining" measurement. The new measurement is compared with the old one by the electronic microprocessor or a simple comparator circuit (not shown) to determine the amount injected. This amount is stored in memory 30. The physician can later review the dosing records stored in memory 30 to assess compliance with the prescribed injection dosing.

The embodiment shown in FIG. 4 operates analogously. The patient takes rotatable plunger syringe 34 and places rotatable cap 40 on field 16 in the manner shown in FIG. 3. This is done before twisting rotatable cap 40 to select the desired amount of medication.

Again, voltage generator 26 applies a well-known voltage V across terminals 42 and 44. This produces a current I in the conductive path which includes potentiometer 54 instead of a resistive strip. Since all parts of the conductive path have negligible resistance in comparison to potentiometer 54 the

SUMMARY, RAMIFICATIONS, AND SCOPE

It can thus be seen that the presented apparatus for determining and recording doses of medicine delivered from an injection syringe is particularly simple in construction. The apparatus is very accurate and inexpensive. In addition this apparatus is user-friendly and recording dose measurements using it requires little time.

The apparatus is particularly well-suited for use by diabetic patients by virtue of being integrated into a blood glucose meter. Of course, the apparatus can also be integrated into other medical devices used in self-care, e.g., reminders and alarm mechanism.

Moreover, the current path established in the syringe can include elements other than those named above. For example, rather than using a resistive strip the bulk of the plunger could be used as the resistive element in measurements. In this case the plunger would be made of an electrically suitable material.

In fact, the apparatus can be use with any type of syringe, including disposable and reusable units with a push plunger or rotatable plunger as long as the conductive path, by virtue of the advance of the plunger changes its resistive, nature.

Therefore, the scope of the invention should be determined, not by examples given, but by the appended claims and their legal equivalents.

I claim:

1. In combination with a syringe, an apparatus for determining and recording the dose of an agent delivered with said syringe, said syringe being of the type comprising:
   a) a barrel for holding said agent;
   b) a plunger arranged inside said barrel for expelling said agent;
   c) a conducting path for conducting an electric current inside said barrel and parallel to said plunger, said conducting path comprising a conductive strip located inside said barrel and oriented parallel along said plunger, a rim on said barrel made of an electrically conducting material and remaining in electric contact with said conductive strip, and an electrically resistive means in the form of a strip whose resistance changes depending on the position of said plunger inside said barrel, said conducting path having a first end and a second end;
   d) an input terminal located on the outside of said syringe and in contact with said first end and with said conducting strip;
   e) an output terminal located on the outside of said syringe and in contact with said second end and with said electrically resistive means;

said apparatus comprising:
   a) a housing;
   b) a field on the outside of said housing, said field having an input contact for contacting said input terminal and an output contact for contacting said output terminal;
   c) a voltage generating means located inside said housing for producing a voltage difference across said input contact and said output contact, thereby causing said electric current to flow through said conducting path when said input contact is contacting said input terminal and said output contact is contacting said output terminal;
   d) an electric response measuring means located inside said housing for measuring said electric current and calculating from said electric current said dose; and
   e) a recording means located inside said housing for recording said dose.

2. The apparatus of claim 1 wherein said electrical response measuring means is an ammeter and said recording means is a digital memory unit.

3. The apparatus of claim 1 wherein said input terminal and said output terminal are located on the cap of said syringe.

4. The apparatus of claim 3 wherein said field is designed for receiving the cap of said syringe, such that said input terminal contacts said input contact and said output terminal contacts said output contact.

5. The apparatus of claim 3 wherein said field is circular.

6. The apparatus of claim 5 wherein said field is bordered by a positioning means for aligning the cap of said syringe, such that said input terminal is in contact with said input contact and said output terminal is in contact with said output contact.

7. The apparatus of claim 3 wherein said input contact is circular and positioned at the center of said field, and said output contact is ring-shaped and positioned concentrically to said input contact.

8. The apparatus of claim 3 wherein said input terminal is circular and positioned at the center of the cap of said syringe, and said output terminal is ring-shaped and positioned concentrically to said input terminal.

9. The apparatus of claim 1 wherein said electrical response measuring means and said recording means are integrated into a blood glucose meter.

10. The apparatus of claim 1 wherein said syringe is a rotatable plunger syringe and said electrically resistive means in the form of a strip comprises a potentiometer mechanically connected to rotate with the cap of said syringe.

* * * * *